US008163235B2

(12) United States Patent
Centanni et al.

(10) Patent No.: US 8,163,235 B2
(45) Date of Patent: Apr. 24, 2012

(54) METHOD FOR REMOVING GASEOUS OR VAPOROUS STERILANTS FROM A SURFACE

(75) Inventors: Michael A. Centanni, Parma, OH (US); Thaddeus J. Mielnik, Concord, OH (US)

(73) Assignee: STERIS Corporation, Mentor, OH (US)

( * ) Notice: Subject to any disclaimer, the term of this patent is extended or adjusted under 35 U.S.C. 154(b) by 0 days.

(21) Appl. No.: 13/297,652

(22) Filed: Nov. 16, 2011

(65) Prior Publication Data

US 2012/0055507 A1 Mar. 8, 2012

Related U.S. Application Data

(62) Division of application No. 12/339,186, filed on Dec. 19, 2008, now Pat. No. 8,092,577.

(51) Int. Cl.
*A61L 2/03* (2006.01)

(52) U.S. Cl. ........... 422/22; 95/77; 96/61; 96/69; 96/94; 96/95; 96/98; 96/223; 96/226; 99/451; 422/186.05; 426/234; 426/237

(58) Field of Classification Search ................ 95/59, 61, 95/77, 78; 96/16, 29, 39–42, 60–63, 69, 96/94–100, 223, 226; 422/22, 122, 186.05, 422/186.06; 313/146; 426/234, 237; 99/451; 204/155, 156, 157.15, 157.3, 158.2
See application file for complete search history.

(56) References Cited

U.S. PATENT DOCUMENTS

| | | | | |
|---|---|---|---|---|
| 2,868,318 | A * | 1/1959 | Perkins et al. | 96/94 |
| 3,056,663 | A | 10/1962 | Maglio et al. | 23/288 |
| 3,313,971 | A | 4/1967 | Nagy | 313/542 |
| 3,363,983 | A | 1/1968 | Roberts | 23/204 |
| 3,654,534 | A | 4/1972 | Fischer | 361/215 |
| 3,696,269 | A | 10/1972 | Hochheiser et al. | 361/231 |
| 4,253,925 | A | 3/1981 | Mason | 204/129 |
| 4,319,979 | A * | 3/1982 | King | 204/660 |

(Continued)

FOREIGN PATENT DOCUMENTS

JP 53-5468 A * 1/1978

(Continued)

OTHER PUBLICATIONS

Henderson, "The Physics Classroom Tutorial, Lesson 4: Electric Fields," 1996-2007, pp. 1-8, www.glenbrook.k12.il.us/GBSSCI/PHYS/CLASS/estatics/u814b.html, last accessed Oct. 27, 2008.

(Continued)

*Primary Examiner* — Richard L Chiesa

(74) *Attorney, Agent, or Firm* — Kusner & Jaffe; Michael A Centanni

(57) ABSTRACT

The present invention provides a method and apparatus for removing chemical sterilant molecules from a medium, such as a carrier gas. In one embodiment, the apparatus includes a housing that defines an internal cavity. The housing has an inlet and an outlet fluidly communicating with the internal cavity. An electrode is dimensioned to be received in the internal cavity of the housing. The electrode is made of a material that is chemically active with respect to molecules of a chemical sterilant and conductive to electricity. The electrode is connected to a source of an electrical charge such that an electrical field gradient is formed in a region of space surrounding the electrode. The electrical field gradient is operable to force the chemical sterilant molecule toward the electrode.

17 Claims, 5 Drawing Sheets

U.S. PATENT DOCUMENTS

| | | | | |
|---|---|---|---|---|
| 4,388,274 | A * | 6/1983 | Rourke et al. | 422/177 |
| 4,574,004 | A | 3/1986 | Schmidt-Ott et al. | 95/79 |
| 4,909,999 | A | 3/1990 | Cummings et al. | 422/298 |
| 4,941,224 | A * | 7/1990 | Saeki et al. | 15/1.51 |
| 5,154,733 | A | 10/1992 | Fujii et al. | 95/57 |
| 5,277,703 | A * | 1/1994 | Sklenak et al. | 95/77 |
| 5,833,740 | A | 11/1998 | Brais | 96/16 |
| 6,159,421 | A | 12/2000 | Fujii | 422/4 |
| 6,187,271 | B1 | 2/2001 | Lee et al. | 422/121 |
| 6,245,126 | B1 | 6/2001 | Feldman et al. | 95/59 |
| 6,342,187 | B1 * | 1/2002 | Jacob et al. | 422/186.05 |
| 6,508,982 | B1 * | 1/2003 | Shoji | 422/22 |
| 6,821,320 | B1 * | 11/2004 | Miyazaki | 96/17 |
| 6,849,192 | B2 | 2/2005 | Nakasaki | 216/64 |
| 6,852,277 | B2 * | 2/2005 | Platt et al. | 422/3 |
| 6,899,748 | B2 * | 5/2005 | Mohamed | 96/3 |
| 6,917,885 | B2 | 7/2005 | Centanni | 702/24 |
| 6,958,088 | B1 * | 10/2005 | Moriyama | 96/39 |
| 7,160,506 | B2 | 1/2007 | Deshpande | 422/4 |
| 7,258,730 | B2 * | 8/2007 | Choi et al. | 96/69 |
| 7,361,212 | B2 * | 4/2008 | Clark et al. | 96/69 |
| 8,092,577 | B2 * | 1/2012 | Centanni et al. | 95/59 |
| 2004/0045442 | A1 * | 3/2004 | Ziya Ramizovich et al. | 96/94 |
| 2004/0226448 | A1 | 11/2004 | Griffiths et al. | 96/67 |
| 2007/0245898 | A1 | 10/2007 | Naito et al. | 96/65 |
| 2007/0283810 | A1 | 12/2007 | Besi | |
| 2008/0310997 | A1 | 12/2008 | Centanni et al. | 422/30 |
| 2010/0154634 | A1 * | 6/2010 | Centanni et al. | 95/77 |

FOREIGN PATENT DOCUMENTS

| | | |
|---|---|---|
| JP | 5-68910 A | 3/1993 |
| JP | 2005-313066 | 11/2005 |
| KR | 10-2002-0001563 | 10/2002 |

OTHER PUBLICATIONS

"Electric Field, Electrical Engineering Training Series," pp. 1-4, Integrated Publishing, www.tpub.com/neets/book10/39i.htm, last accessed Feb. 27, 2008.

Tatum, J.B., "Physics Topics, Electricity and Magnetism, Chapter 3: Dipole and Quadrupole Moments," pp. 1-17, http://www.astro.uvic.ca/~tatum/elmag/em3.pdf, last accessed Mar. 9, 2009.

"Hydrogen peroxide," Wikipedia, pp. 1-12, http://en.wikipedia.org/wiki/Hydrogen_peorxide, last accessed Sep. 10, 2007.

U.S. Appl. No. 12/339,186, filed Dec. 19, 2008.

* cited by examiner

METHOD FOR REMOVING GASEOUS OR VAPOROUS STERILANTS FROM A SURFACE

RELATED APPLICATIONS

This application is a divisional of U.S. application Ser. No. 12/339,186, filed Dec. 19, 2008, (now U.S. Pat. No. 8,092,577), and is hereby fully incorporated herein by reference.

FIELD OF THE INVENTION

The present invention generally relates to a method and apparatus for removing chemical sterilant molecules from a medium, and more particularly, to a method and apparatus for removing gaseous or vaporous chemical sterilant molecules from a carrier gas or surface of an object, wherein the chemical sterilant molecules have an induced electrical dipole moment or a permanent electrical dipole moment.

BACKGROUND OF THE INVENTION

Decontamination systems typically use gaseous chemical sterilants, e.g., ozone, or vaporous chemical sterilants, such as, vaporized hydrogen peroxide ("VHP"), to deactivate biocontamination and/or neutralize chemical contamination in a region, such as hotel rooms and motor vehicles, and on internal and external surfaces of food and beverage containers (e.g., bottles). Such chemical sterilants are also typically used to deactivate biocontamination harbored on internal or external surfaces of medical instruments and other items used in the health care industry.

A decontamination cycle of decontamination systems for decontaminating a region (such as a room) typically includes an exposure phase wherein the chemical sterilant is introduced into the region and maintained at a predetermined concentration for a predetermined period of time. Following the exposure phase, the decontamination system performs an aeration phase wherein the concentration of the chemical sterilant is reduced. A destroyer in the decontamination system is typically used to reduce the concentration of the chemical sterilant. The destroyer includes a material that is chemically active (e.g., destructive or reactive) with respect to molecules of the chemical sterilant as, by way of example and not limitation, by catalysis, physical forces, electrical forces or chemical reaction. The aeration phase continues until the concentration of the chemical sterilant within the region is reduced to below a predetermined threshold level.

When decontaminating a room, such as a hotel room, with VHP, the concentration of VHP within the room needs to be reduced to below 1 part per million (1 ppm), especially, if humans are to enter the room without protective equipment. It is therefore desirable that the concentration of the chemical sterilant in the room be reduced to below the threshold value of 1 ppm as quickly as possible. With existing systems, it is difficult to reduce the concentration of VHP within the room to below the 1 ppm threshold level in a reasonable amount of time.

One factor that influences the ability of present decontamination systems to quickly reduce the concentration of VHP in the room is the efficiency of the destroyer in the decontamination system. Presently available destroyers for VHP are constructed with materials that are catalytic to the destruction of VHP, i.e., a catalyst. The VHP molecules are catalytically destroyed upon contact with the surface of the catalytic material. However, during operation of existing decontamination systems, some of the VHP molecules simply pass through the destroyer without making contact with the catalytic material.

This is especially true at low concentrations of VHP. In a closed-loop system, these VHP molecules are then re-injected into the region only to be evacuated from the region and passed through the destroyer again. In some situations, the VHP molecule may pass through the destroyer several times before the VHP molecule contacts the catalytic material in the destroyer. Therefore, it would be advantageous to have a method and apparatus that minimizes the number of VHP molecules that are re-injected into the air in the room.

It is also believed that part of the difficulty in quickly reducing the concentration of the VHP in the room is tied to the sorption of VHP molecules by the surface of the walls that define the room and the surface of other articles in the room. The VHP molecules that are disposed on or in the surfaces must first diffuse into the air before they can be circulated through the destroyer. Typically, these VHP molecules diffuse into the air as a result of thermal effects or because of a concentration gradient that exists between the surfaces and the air. It would be advantageous to have a method and apparatus that exerts a force on the VHP molecules on or in the surfaces to accelerate their diffusion into the air.

Similar problems arise when VHP is used to decontaminate containers used in the food and beverage industry (e.g., bottles and food containers). It is believed that VHP is adsorbed to the surfaces of the containers. Desorption and adsorption of VHP molecules from a surface is a dynamic process. Without an external force to pull the VHP molecules from the surface of the container, some of the VHP molecules will desorb from the surface while others will adsorb back onto the surface of the container. It would thus be advantageous to force the desorption of VHP molecules from the surface of the container and destroy the VHP molecules before they adsorb back onto the surface of the container.

The present invention overcomes these and other problems and provides a method and apparatus for removing chemical sterilant from a medium by forcing the motion of a chemical sterilant molecule that has an induced or permanent electrical dipole moment.

SUMMARY OF THE INVENTION

In accordance with one embodiment of the present invention, there is provided an apparatus for removing chemical sterilant molecules from a carrier gas. The apparatus includes a housing that defines an internal cavity. The housing has an inlet and an outlet fluidly communicating with the internal cavity. An electrode is dimensioned to be received in the internal cavity of the housing. The electrode is made of a material that is chemically active with respect to molecules of a chemical sterilant and conductive to electricity. The electrode is connected to a source of an electrical charge such that an electrical field gradient is formed in a region of space surrounding the electrode. The electrical field gradient is operable to force the chemical sterilant molecules toward the electrode.

In accordance with another aspect of the present invention, there is provided a method for removing chemical sterilant molecules from a carrier gas flowing through a housing. The housing defines an internal cavity. The housing has an inlet and an outlet in fluid communication with the internal cavity. The method includes the steps of (a) applying an electrical charge to an electrode located in an internal cavity of a housing, the electrode formed of a material that is chemically active with respect to molecules of a chemical sterilant and conductive to electricity, the charged electrode forming an electrical field gradient in a region of space surrounding the electrode; and (b) flowing the carrier gas through the internal cavity, wherein the electrical field gradient forces the chemical sterilant molecule toward the electrode.

In accordance with still another aspect of the present invention, there is provided method for removing chemical sterilant molecules from a surface. The method includes the steps of (a) applying an electrical charge to an electrode located near a surface, the electrode formed of a material that is chemically active with respect to molecules of a chemical sterilant and conductive to electricity, the charged electrode forming an electrical field gradient in the region of space that surrounds the charged rod; and (b) moving the electrode relative to the surface.

In accordance with yet another aspect of the present invention, there is provided an apparatus for removing chemical sterilant molecules from a surface of a container. The apparatus includes a rod made of a material that is chemically active with respect to molecules of a chemical sterilant and conductive to electricity. The electrode is connected to a source of an electrical charge such that an electrical field gradient is formed in the region of space that surrounds the charged rod. The electrical field gradient is operable to force the chemical sterilant molecules toward the rod.

In accordance with yet another aspect of the present invention a bladder is disposed on a distal end of the rod. The bladder is expandable between a first, collapsed state and a second, expanded state. The bladder is embedded with elements made of a material that is chemically active with respect to the chemical sterilant molecules and conductive to electricity.

An advantage of the present invention is the provision of a method and apparatus for removing gaseous or vaporous chemical sterilant molecules from a medium, the method and apparatus having a charged electrode operable to attract gaseous or vaporous chemical sterilant molecules.

Another advantage of the present invention is the provision of a method and apparatus as described above wherein a destroyer includes the charged electrode.

Yet another advantage of the present invention is the provision of a method and apparatus as described above wherein the destroyer is operable to reduce the number of gaseous or vaporous chemical sterilant molecules that are re-injected into a region.

Another advantage of the present invention is the provision of a method and apparatus as described above that facilitates the removal of gaseous or vaporous chemical sterilant molecules from a region.

Another advantage of the present invention is the provision of a method and apparatus as described above that facilitates the removal of gaseous or vaporous chemical sterilant molecules from a surface.

Yet another advantage of the present invention is the provision of a method and apparatus as described above that reduces the time required to remove gaseous or vaporous chemical sterilant molecules from a medium.

Yet another advantage of the present invention is the provision of a method and apparatus as described above that reduces the time required to remove gaseous or vaporous chemical sterilant molecules from a container, such as a bottle.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, one embodiment of which will be described in detail in the specification and illustrated in the accompanying drawings which form a part hereof, and wherein.

DETAILED DESCRIPTION OF THE INVENTION

Figure 1:
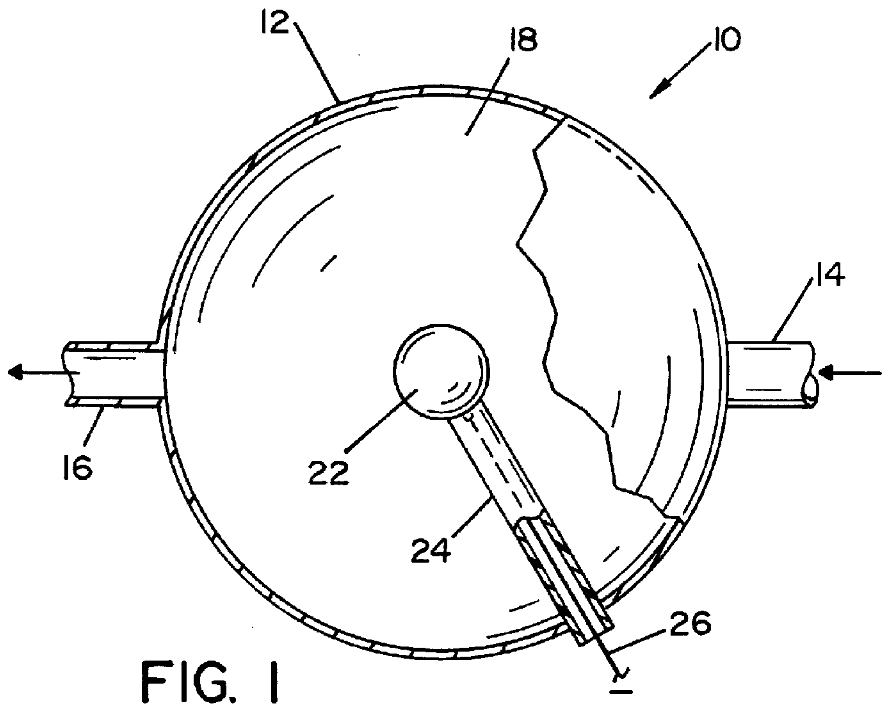
FIG. 1 is a partially sectioned, side view of a destroyer in accordance with a first embodiment of the present invention.

Referring now to the drawings wherein the showings are for the purpose of illustrating a preferred embodiment of the invention only, and not for the purpose of limiting the same, FIG. 1 shows a destroyer 10 for removing a chemical sterilant, such as vaporized hydrogen peroxide ("VHP") or ozone, from a carrier gas. Destroyer 10 is generally comprised of a housing 12 and an electrode 22.

Housing 12 has a generally spherical shape and defines an internal cavity 18. Housing 12 also includes an inlet 14 and an outlet 16 that fluidly communicate with internal cavity 18. In the embodiment illustrated in FIG. 1, housing 12 is formed of an electrically conductive material (i.e., a conductor or semiconductor material). It is contemplated that if housing 12 is formed of an electrically conductive material that housing 12 may also be connected to a source of electrical charge (not shown). It is also contemplated that housing 12 may alternatively be formed of a non-conductive material.

In one embodiment, housing 12 is made of a material that is chemically active (e.g., destructive or reactive) with respect to molecules of the chemical sterilant as, by way of example and not limitation, by catalysis, physical forces, electrical forces, or chemical reaction. For example, housing 12 may be formed of glass frits, precious metals, copper, silver or a transition metal including, but not limited to, platinum and palladium and transition metal oxides including, but not limited to, oxides of manganese and manganese dioxide that is electrically conductive and catalytic to the destruction of VHP. The catalytic destruction of VHP results in the formation of oxygen and water. Housing 12 may also be formed of carbon or a carbon-containing material. The reaction of carbon with ozone results in the formation of carbon dioxide and carbon monoxide.

Electrode 22 is disposed within internal cavity 18 of housing 12. In the embodiment shown, electrode 22 is generally spherical in shape. Electrode 22 may be formed as a solid or a hollow sphere. Electrode 22 is supported within internal cavity 18 by a first end of a support tube 24. A second end of support tube 24 extends through a wall of housing 12. A conductive wire or cable 26 extends through support tube 24, wherein a first end of wire 26 is electrically connected to electrode 22 and a second end of wire or cable 26 is electrically connected to a source of electrical charge (not shown). The source of electrical charge is at a negative or positive electrical potential. In the illustrated embodiment, the source of electrical charge is at a negative potential.

Electrode 22 is comprised of a material that is conductive (i.e., a conductor or semi-conductor material) and is chemically active (e.g., destructive or reactive) with respect to molecules of the chemical sterilant as, by way of example and not limitation, by catalysis, physical forces, electrical forces, or chemical reaction. For example, electrode 22 may be formed of glass flits, copper, a precious metal including, but not limited to, silver or a transition metal including, but not limited to, platinum and palladium and transition metal oxides including, but not limited to, oxides of manganese and manganese dioxide that is electrically conductive and catalytic to the destruction of VHP. As indicated above, the catalytic destruction of VHP results in the formation of oxygen and water. It is also contemplated that electrode 22 may be formed of carbon or a carbon-containing material. As discussed above, the reaction of carbon with ozone results in the formation of carbon dioxide and carbon monoxide.

During operation of the present invention, a carrier gas, such as air, is circulated through internal cavity 18. The carrier gas includes a plurality of chemical sterilant molecules, such as VHP or ozone molecules, therein. The carrier gas flows into inlet 14, through internal cavity 18 and exits through outlet 16. Electrode 22 is charged with a negative or positive charge such that an electric field is created. In the embodiment wherein housing 12 is connected to a source of electrical charge, housing 12 is charged to an electrical potential opposite the charge on electrode 22. For example, if electrode 22 is negatively charged (as shown in FIG. 1) then housing 12 is positively charged. In the embodiment shown, the electric field associated with electrode 22 points inwardly toward a surface of electrode 22. The strength of the electric field associated with electrode 22 varies according to the following equation:

$$E = \frac{kQ}{d^2} \quad (1)$$

Where:

$k=9.0\times10^9\ Nm^2/C^2$

Q=excess charge of electrode 22 d=distance from electrode 22

In this respect, the strength of the electric field varies inversely to the square of the distance from electrode 22. In other words, the strength of the electric field at a first point near a surface of electrode 22 is greater than the strength of the electric field at a second point farther away from the surface of electrode 22. Because the strength of the electric field varies radially from electrode 22, the electric field created by electrode 22 is commonly called a "non-uniform" field. In the embodiment shown in FIG. 1, housing 12 and electrode 22 are generally spherical in shape. It is contemplated that housing 12 and electrode 22 may have other shapes or geometries as long as the electric field associated with electrode 22 is non-uniform.

According to the present invention, the chemical sterilant molecules in the carrier gas have either a permanent electric dipole moment or possess an induced electric dipole moment, the induced electric dipole moment produced when the molecules are placed in a non-uniform electric field. In the instance wherein the chemical sterilant molecules do not have a permanent dipole moment, the non-uniform electric field polarizes the chemical sterilant molecules.

When molecules that have a permanent or induced electric dipole moment are placed in a non-uniform electric field, one end of a chemical sterilant molecule is forced toward electrode 22 and the other end of the chemical sterilant molecule is forced away from electrode 22. For example, if electrode 22 has a negative charge, a positively charged end of the chemical sterilant molecule is forced toward electrode 22, whereas a negatively charged end of the chemical sterilant molecule is forced away from electrode 22. If electrode 22 is positively charged, the negatively charged end of the sterilant molecule is forced toward electrode 22 and the other positively charged end of the sterilant molecule is forced away from electrode 22. For both a chemical sterilant molecule that has a permanent dipole moment and a chemical sterilant molecule that has an induced dipole moment, the oppositely charged ends of the chemical sterilant molecule are separated by a distance "dx." It is believed that the force the electric field exerts on the ends of the chemical sterilant molecules is given by the equation:

$$F=qE \quad (2)$$

Where:

q=quantity of charge on one end of sterilant chemical molecule

E=strength of the electric field given in Equation 1

The force on the end of the chemical sterilant molecule closest to electrode 22 is directed toward electrode 22 and is given by the equation:

$$F_1 = q\left(\frac{kQ}{d^2}\right) \quad (3)$$

The force on the end of the chemical sterilant molecule farthest from electrode 22 is directed away from electrode 22 and is given by the equation:

$$F_2 = q\left(\frac{kQ}{(d+dx)^2}\right) \quad (4)$$

Thus, the net force on the chemical sterilant molecule towards electrode 22 is:

$$F_{net} = F_1 - F_2 = kqQdx\left(\frac{2d+dx}{d^2(d+dx)^2}\right) \quad (5)$$

As described above, electrode 22 of the present invention is provided to create an electric field such that a net force on a chemical sterilant molecule in destroyer 10 drives the chemical sterilant molecule toward electrode 22. As indicated above, electrode 22 includes a material that is chemically active (e.g., destructive or reactive) with respect to a chemical sterilant molecule when the chemical sterilant molecule contacts electrode 22. After the chemical sterilant molecules contacts electrode 22, the carrier gas and the products resulting from the sterilant's contact with electrode 22 exit destroyer 10 through outlet 16. In this respect, the present invention provides a method and apparatus for removing chemical sterilant molecules from a medium, such as a carrier gas.

Figure 2:
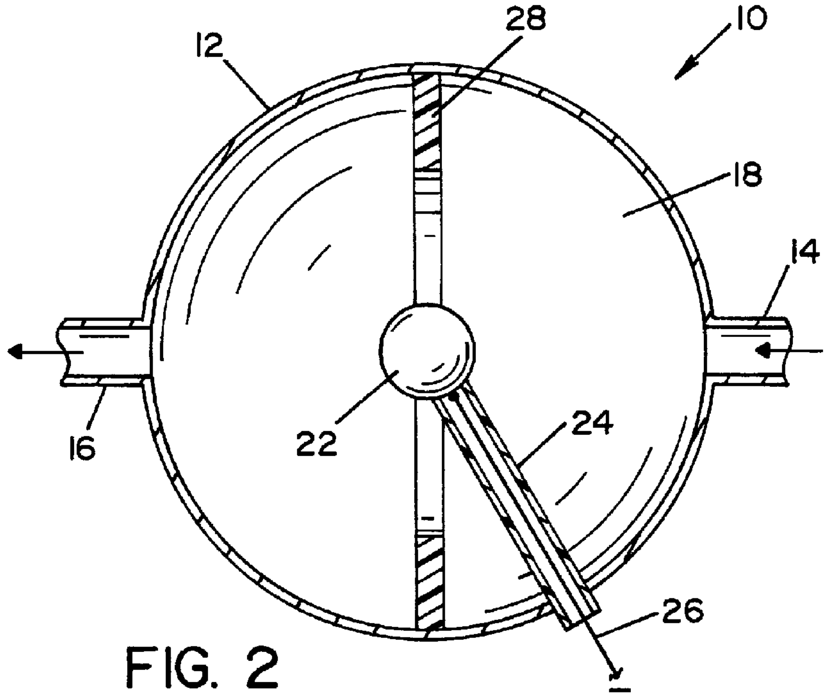
FIG. 2 is a sectioned side view of the destroyer shown in FIG. 1 modified to include an insert for promoting turbulent fluid flow.

FIG. 2 illustrates another embodiment of destroyer 10, wherein the destroyer is modified to include an insert 28 disposed in internal cavity 18 of housing 12. Insert 28 is designed to disrupt any streamlines that are formed as the carrier gas flows through destroyer 10. It is believed that insert 28 will promote the production of turbulence (i.e., turbulent fluid flow) within cavity 18. The turbulence helps to drive chemical sterilant molecules within cavity 18 toward electrode 22. It is also believed that the turbulence produced in cavity 18 will increase the residence time of chemical sterilant molecules within internal cavity 18. The increase in residence time provides more time for the electric field created by electrode 22 to force the chemical sterilant molecules towards electrode 22.

Figure 3:
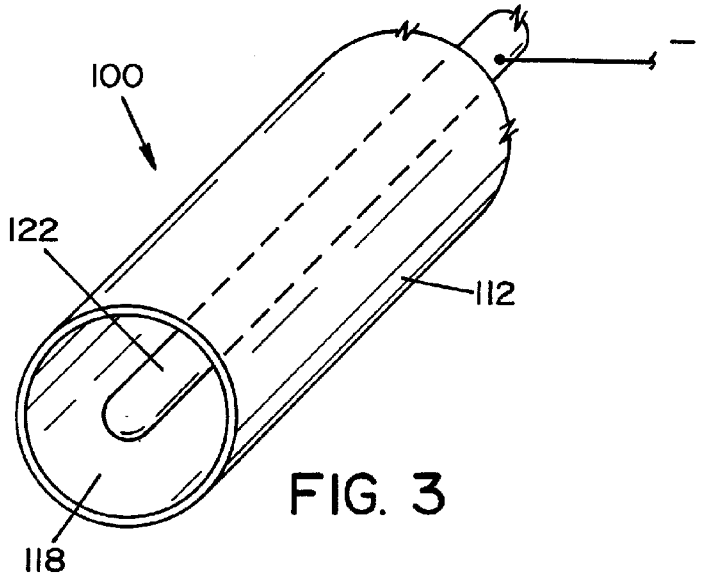
FIG. 3 is a perspective view of a destroyer in accordance with another embodiment of the present invention.
Figure 4:
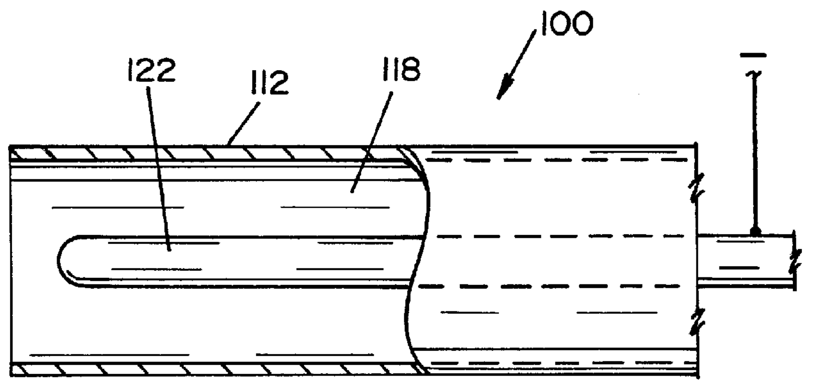
FIG. 4 is a partially sectioned, side view of the destroyer shown in FIG. 3.

Referring now to FIGS. 3 and 4, a destroyer 100 according to an alternative embodiment will be described. Destroyer 100 includes a housing 112 and an electrode 122. Housing 112 is a cylindrical element that defines a cylindrical internal cavity 118. Housing 112 may be formed of the same materials as discussed above in connection with housing 12. Like housing 12 described above, housing 112 may be connected to a source of electrical charge when housing 112 is made of an electrically conductive material.

Electrode 122 is disposed in internal cavity 118 of housing 112. In the embodiment shown, electrode 122 is a rod shaped member. Electrode 122 may be formed of the same materials as described above in connection with electrode 22. Like electrode 22, electrode 122 is connected to a source of electrical charge (not shown) at a positive or negative electric potential. In the embodiment shown, electrode 122 is connected to a source of electrical charge at a negative electrical potential.

In the embodiment shown, electrode 122 is disposed in housing 112 such that a principal axis of housing 112 and a principal axis of electrode 122 are generally coincident. It is also contemplated that electrode 122 may be disposed in housing 112 such that the principal axis of electrode 122 is parallel to, but displaced from, the principal axis of housing 112.

During operation of destroyer 100, a carrier gas, containing chemical sterilant molecules, is injected into one end of destroyer 100. The carrier gas flows in a direction that generally parallels the longitudinal axis of electrode 122 and housing 112. In a similar fashion as described above, the electric field gradient associated with electrode 122 forces the chemical sterilant molecules in the carrier gas toward electrode 122. After the chemical sterilant molecules contact electrode 122, the carrier gas and the products resulting from the sterilant's contact with electrode 122 exit destroyer 100 through another end of destroyer 100. As a result, the concentration of chemical sterilant molecules in the carrier gas is reduced.

Figure 4A:
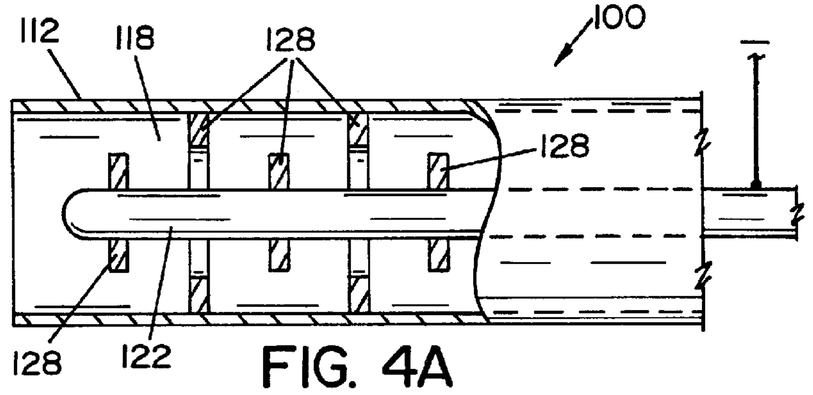
FIG. 4A is a partially sectioned, side view of the destroyer shown in FIG. 4 modified to include a plurality of inserts for promoting turbulent fluid flow.

FIG. 4A illustrates another embodiment of destroyer 100, wherein a plurality of inserts 128 are disposed between housing 112 and electrode 122. Similar to insert 28, inserts 128 are designed to disrupt any streamlines that are formed as the carrier gas flows through destroyer 100. In addition, inserts 128 are designed to increase the residence time of chemical sterilant molecules within internal cavity 118. As indicated above, an increase in residence time will provide more time for the electric field to force the chemical sterilant molecules toward electrode 122.

Figure 5:
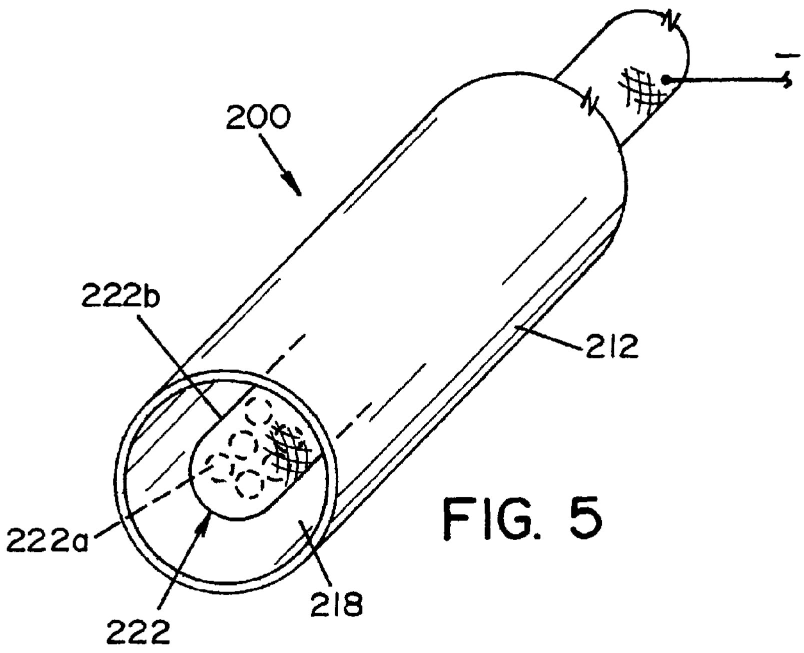
FIG. 5 is a perspective view of a destroyer in accordance with yet another embodiment of the present invention.
Figure 6:
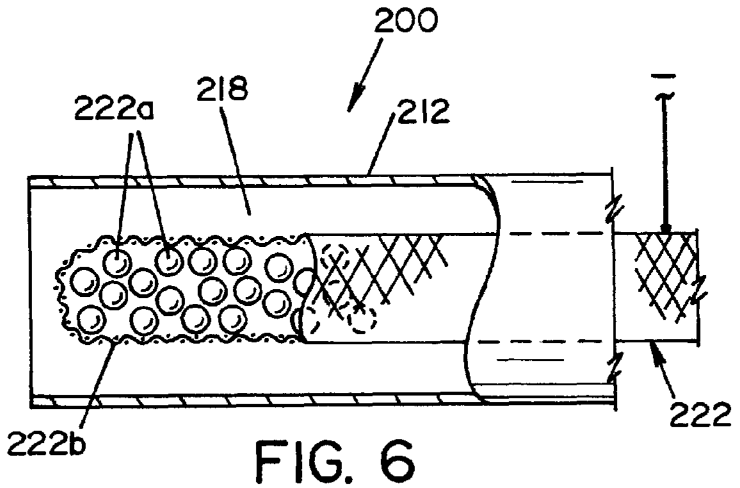
FIG. 6 is a partially sectioned, side view of the destroyer shown in FIG. 5.

Referring now to FIGS. 5-6, yet another embodiment of the present invention is shown. Destroyer 200 comprises a housing 212, similar to housing 112, and an electrode 222. Housing 212 is a cylindrical element that defines a cylindrical internal cavity 218. Housing 212 may be formed of the same materials as discussed above in connection with housing 12. Like housing 12 described above, housing 212 may be connected to a source of electrical charge when housing 212 is made of an electrically conductive material.

Electrode 222 is disposed in internal cavity 218. Electrode 222 is comprised of a plurality of elements 222*a* and a mesh element 222*b*. In the embodiment shown, elements 222*a* are spherically shaped bodies. It is also contemplated that elements 222*a* may take the form of fibers, whiskers, flakes or the like, and combinations thereof.

Elements 222*a* and mesh element 222*b* may be formed of the same materials as discussed above in connection with electrode 22. Elements 222*a* and mesh element 222*b* will provide additional surface area to contact chemical sterilant molecules in the carrier gas circulated through destroyer 200. In this respect, the likelihood that the chemical sterilant molecules will contact a material that is chemically active with respect to molecules of the chemical sterilant is increased. Like electrode 22, elements 222*a* and mesh element 222*b* are connected to a source of electrical charge (not shown) at a positive or negative potential. In the embodiment shown, elements 222*a* and mesh member 222*b* are connected to a source of a negative electrical charge (not shown). As a result, a non-uniform electric field associated with elements 222*a* and mesh element 222*b* forces sterilant molecules toward elements 222*a* and mesh element 222*b*. After the chemical sterilant molecules contact elements 222*a* or mesh element 222*b*, the carrier gas and the products resulting from such contact therewith exit destroyer 200 through another end of destroyer 200. As a result, the concentration of chemical sterilant molecules in the carrier gas is reduced.

Figure 7:
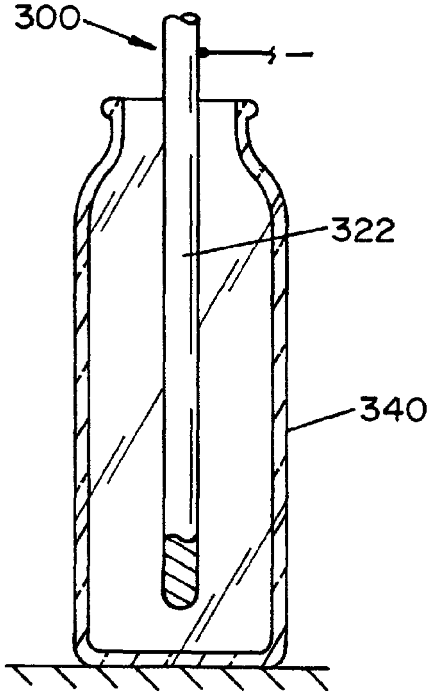
FIG. 7 is a partially sectioned, side view of a destroyer wand in accordance with still another embodiment of the present invention, wherein the wand is located within a bottle.
Figure 8:
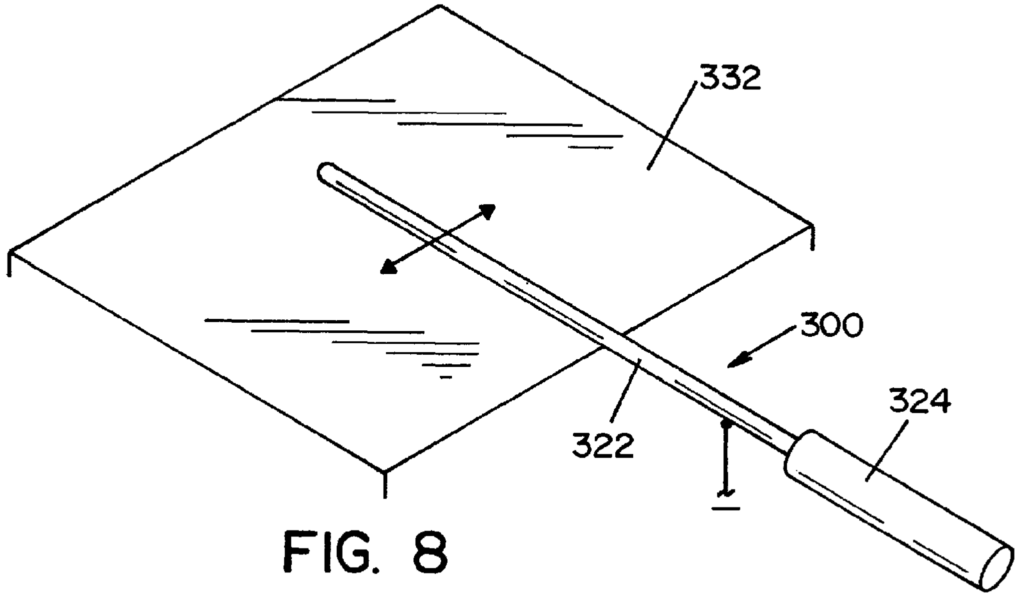
FIG. 8 is a perspective view of the destroyer wand shown in FIG. 7, wherein the destroyer wand is located near a surface.

As stated above, chemical sterilants are also used to decontaminate surfaces and containers used in the food and beverage industry (e.g., bottles and food containers). FIG. 7 illustrates an embodiment of the present invention that provides a method and apparatus to force the desorption of sterilant molecules from the surface of a container and destroy the sterilant molecules before they adsorb back onto the surface of the container. FIG. 8 illustrates an embodiment of the present invention that provides a method and apparatus to force the desorption of sterilant molecules from a surface and destroy the sterilant molecules before they absorb back onto the surface.

A destroyer wand 300 is comprised of a generally rod-shaped electrode 322 and an insulated handle portion 324, as illustrated in FIG. 8. Electrode 322 may be formed of the same materials as described above in connection with electrode 22. Like electrode 22, electrode 322 is connected to a source of electrical charge (not shown) at a positive or negative potential. In the embodiment shown, electrode 322 is connected to a source of electrical charge at a negative electrical charge.

With reference to FIG. 7, operation of destroyer wand 300 will be described in connection with the removal of sterilant molecules from the internal surface of a container 340. The dimensions (e.g. length and diameter) of destroyer wand 300 may vary depending upon the dimensions of the container used in connection with destroyer wand 300. It should be appreciated that container 340 is exemplary of the types of containers suitable for use in connection with destroyer wand 300, and is not intended to limit the scope of the present invention. Prior to inserting destroyer wand 300 into container 340, an inner surface of container 340 is exposed to a chemical sterilant. Afterwards, the distal end of destroyer wand 300 is inserted into the internal cavity of container 340. Electrode 322 is then charged. Like electrode 22, an electric field gradient is produced by electrode 322 wherein the electric field is strongest near the outer surface of electrode 322. Chemical sterilant molecules on a side wall of container 340 are forced to electrode 322. Upon contact, the chemical sterilant molecules form products, as described above. As a result, chemical sterilant molecules are removed from the side wall of container 340. The present embodiment, therefore, facilitates the removal of a chemical sterilant molecule from an internal cavity and side wall of container 340.

It is contemplated that destroyer wand 300 may be used on an assembly line to deactivate the chemical sterilant molecules in a container. In this respect, destroyer wand 300 is inserted into one container, energized to force any chemical sterilant molecules therein toward electrode 322. Destroyer wand 300 is then withdrawn and inserted into another container. Destroyer wand 300 may be manually inserted and withdrawn from containers or mechanically connected with automation machinery. Destroyer wand 300 finds particular application in processing plants wherein a plurality of beverage bottles or food containers are decontaminated.

Referring now to FIG. 8, destroyer wand 300 may also be placed in close proximity to a surface 332 (e.g., a wall). As illustrated, destroyer wand 300 is drawn across surface 332. In a similar fashion as described above, a non-uniform electric field associated with electrode 322 exerts a force on chemical sterilant molecules adsorbed on surface 332 or absorbed within the material below surface 332. Upon contact with destroyer wand 300, the chemical sterilant molecules faun products, as described above. As a result, chemical sterilant molecules are removed from surface 332 and from the material beneath surface 332.

Figure 9A:
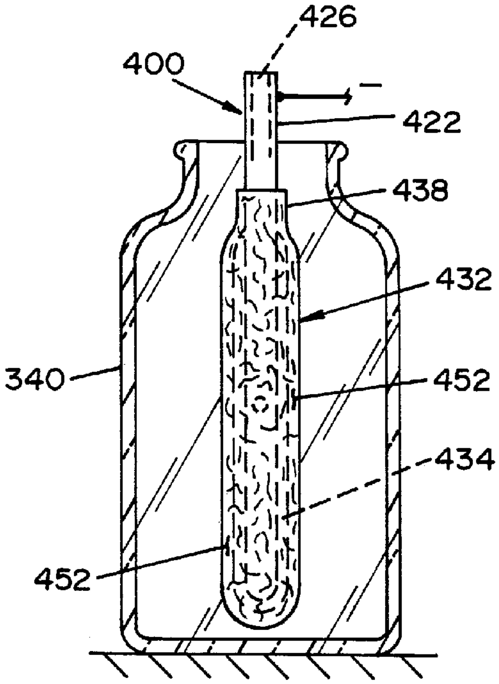
FIG. 9A is a partially sectioned, side view of a destroyer wand and bladder according to another embodiment of the present invention, wherein the bladder is shown in a collapsed state.

In an alternative embodiment of the present invention, as illustrated in FIG. 9A, a destroyer wand 400 is comprised of an electrode 422, a bladder 432 and an insulated gripping portion (not shown). Electrode 422 is a generally cylindrically-shaped element. An inner cavity 426 extends axially along a portion of electrode 422. Cavity 426 fluidly communicates with a source of pressurized gas. A hole 428 extends through a side wall of electrode 422 to fluidly communicate with cavity 426. Electrode 422 is formed of the same materials as described above in connection with electrode 22. Like electrode 22, electrode 422 is connected to a source of electrical charge (not shown) at a positive or negative potential. In the embodiment shown, electrode 422 is connected to a source of electrical charge at a negative electrical charge.

Figure 9B:
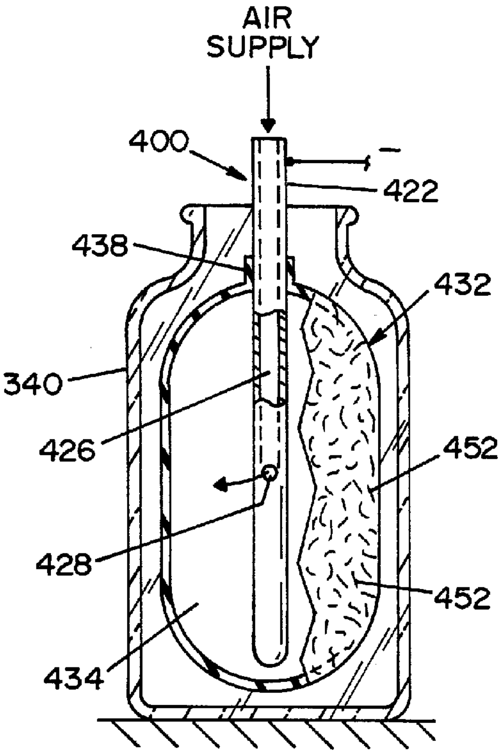
FIG. 9B is a partially second, side view of the destroyer wand of FIG. 9A, wherein the bladder is shown in an expanded state.

Bladder 432 is a generally cylindrical-shaped element with an internal cavity 434. Bladder 432 includes an opening through one end thereof. A flange 438 is formed around the opening. Bladder 432 is formed of a polymer material with conductive elements 452 embedded therein. The concentration of elements 452 is equal to or greater than the percolation threshold. By way of example and not limitation, conductive elements 452 may take the form of whiskers, fibers, flakes, spheres or the like, and combinations thereof. Elements 452 are also comprised of a material that is chemically active (e.g., destructive or reactive) with respect to molecules of the chemical sterilant as, by way of example and not limitation, by catalysis, physical forces, electrical forces, or chemical reaction. Elements 452 are electrically connected to electrode 422. Bladder 432 is expandable between a first, deflated state, as shown in FIG. 9A, and a second, inflated state, as shown in FIG. 9B, as shall be described in greater detail below.

Bladder 432 is dimensioned to be disposed around a distal end of electrode 422. Flange 438 is dimensioned to sealingly engage with an outer surface of electrode 422. Hole 428 is positioned to be in fluid communication with internal cavity 434 when bladder 432 is disposed around electrode 422.

During operation, destroyer wand 400 is inserted into container 340 such that bladder 432 is disposed in the internal cavity of container 340, as illustrated in FIG. 9A. Gas from a source of pressurized gas flows into internal cavity 434 thereby causing bladder 432 to expand from the first, deflated state to the second, inflated state, as illustrated in FIG. 9B. In one embodiment, the gas is air. Bladder 432 is designed such that when bladder 432 is inflated, bladder 432 is in close proximity to the side wall of container 340 without contacting the side wall of container 340. Electrode 422 and conductive elements 452 are then electrically charged to force chemical sterilant molecules on the side wall of container 340 and within the space therebetween toward elements 452. Upon contact with elements 452, the chemical sterilant molecules form products, as described above. As a result, chemical sterilant molecules are removed from the side wall of container 340. It is contemplated that bladder 432 may have other shapes as long as the electric field associated with electrode 422 is non-uniform. This embodiment of the present invention finds particular utility when a diameter of the opening of container 340 is significantly smaller than a diameter of the side wall of container 340 or when the side wall of container 340 has an irregular shape.

It is also contemplated that other embodiments of the present invention may include various combinations of the embodiments described above. For example, electrodes 22, 122, 322 and 422 may also be comprised of elements similar to elements 222*a* and mesh element 222*b* of electrode 222. Destroyer 200 may include inserts similar to inserts 128 of destroyer 100.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A method for removing sterilant molecules from a surface, said method comprising the steps of:

applying an electrical charge to an electrically conductive electrode to form an electric field gradient in a region of space surrounding the electrode, said electrode comprised of a material that is chemically active with respect to the sterilant molecules;

locating the electrode near the surface; and moving the electrode relative to the surface.

2. A method according to claim 1, wherein said surface is a surface of a wall defining an internal cavity of a container.

3. A method according to claim 2, wherein said electrode is located at a distal end of a wand, said step of moving the electrode relative to the surface includes:

inserting and withdrawing the distal end of the wand into/from said internal cavity to remove the sterilant molecules from the surface of said wall.

4. A method according to claim 2, wherein said container is a food or beverage container.

5. A method according to claim 1, wherein said surface is a generally planar surface.

6. A method according to claim 5, wherein said generally planar surface is a surface of a wall.

7. A method according to claim 1, wherein said electrode is located at a distal end of a wand.

8. A method according to claim 7, wherein said wand is hand held.

9. A method according to claim 7, wherein said wand is mechanically connected with automated machinery for moving the wand relative to the surface.

10. A method according to claim 7, wherein said step of moving the electrode relative to the surface includes:

drawing the distal end of the wand across said surface.

11. A method according to claim 1, wherein said electric field gradient exerts a force on chemical sterilant molecules adsorbed on said surface or absorbed within a material below said surface.

12. A method according to claim 1, wherein said electrode is comprised of a mesh element enclosing at least one of the following: spherically shaped bodies, fibers, whiskers, or flakes.

13. A method according to claim 1, wherein said sterilant molecules are comprised of vaporized hydrogen peroxide.

14. A method according to claim 1, wherein said sterilant molecules are comprised of ozone.

15. A method according to claim 1, wherein said material is a transition metal.

16. A method according to claim 1, wherein said material is copper.

17. A method according to claim 1, wherein said material is silver.

* * * * *